United States Patent [19]
Bernardi

[11] Patent Number: 5,959,149
[45] Date of Patent: Sep. 28, 1999

[54] METHOD FOR THE PURIFICATION OF DINITROANILINES

[75] Inventor: Gianluca Bernardi, Brescia, Italy

[73] Assignee: Finchimica S.p.A., Brescia, Italy

[21] Appl. No.: 09/113,998

[22] Filed: Jul. 10, 1998

[30]     Foreign Application Priority Data

Jul. 14, 1997 [IT] Italy ................................. T097A0636

[51] Int. Cl.⁶ .................................................. C07C 85/11
[52] U.S. Cl. ........................... 564/437; 564/438; 564/441
[58] Field of Search ..................................... 564/437, 438, 564/441

[56]            References Cited

U.S. PATENT DOCUMENTS

| 4,134,917 | 1/1979 | Ross et al. . |
| 4,226,789 | 10/1980 | Eizember et al. . |
| 4,391,992 | 7/1983 | Daniels et al. . |

FOREIGN PATENT DOCUMENTS

| 0 024 503 A1 | 3/1981 | European Pat. Off. . |
| 0 049 384 A1 | 4/1982 | European Pat. Off. . |
| 0 024 503 B1 | 6/1983 | European Pat. Off. . |
| 0 049 384 B1 | 3/1985 | European Pat. Off. . |
| 0 847 984 A1 | 6/1998 | European Pat. Off. . |
| 28 31 119 A1 | 2/1979 | Germany . |

OTHER PUBLICATIONS

EP Search Report, Finchimica S.p.A., Jan. 14, 1999.

*Primary Examiner*—Brian M. Burn
*Attorney, Agent, or Firm*—Donald L. Rhoads; Todd J. Tiberi; Kramer Levin Naftalis & Frankel LLP

[57]            ABSTRACT

A method for the purification of dinitroanilines having herbicidal activity by means of the known reactions of denitrosation using acid, and denitration in a neutral or basic environment in the presence of a phase-transfer catalyst, wherein:

the denitrosation reaction is effected on the dinitration mixture containing the dinitroaniline of interest and the corresponding unwanted N-nitroso- and N-dinitroaniline impurities, and in the absence of solvent, the denitration reaction is conducted sequentially to the denitrosation reaction in the same reactor with the addition to the denitrosation product as such of an aqueous base, and of the said phase-transfer catalyst.

6 Claims, No Drawings

METHOD FOR THE PURIFICATION OF DINITROANILINES

DESCRIPTION

The present invention concerns a method for the purification of dinitroanilines having herbicidal activity by way of the known reactions of denitrosation with acid, and denitration in a neutral or basic environment in the presence of a phase-transfer catalyst.

Dinitroanilines having herbicidal activity, the purification of which is addressed by the method of the invention, have the general formula:

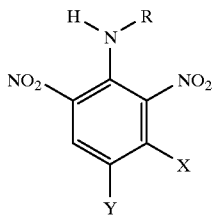

in which R is a linear or preferably branched $C_1$–$C_6$ alkyl group, a $C_4$–$C_6$ cycloalkyl group, a $C_1$–$C_4$ monohaloalkyl group or a $C_1$–$C_4$ alkoxy ($C_2$–$C_4$) alkyl group, Y is a $C_1$–$C_4$ alkyl group, a halogen or $CF_3$, and X is hydrogen, a halogen, a $C_1$–$C_4$ alkyl group, a $C_1$–$C_4$ alkoxy group, a $C_1$–$C_6$ monohaloalkyl group or a $C_1$–$C_4$ alkoxy ($C_1$–$C_6$) alkyl group. The compounds in which R is 1-ethylpropyl, Y is methyl or isopropyl and X is methyl or methoxymethyl are particularly interesting, specifically, the compound N-alkyl-2,6-dinitro-3,4-dimethylbenzenamine, known commercially as Pendimethalin.

The aforesaid compounds are obtained by the known method of nitration or dinitration of substituted anilines. It is known that nitration leads to the formation of unwanted by-products constituted by the N-nitro-dinitroanilines (N,2,6-trinitroanilines) and the N-nitroso-dinitroanilines, which must be removed from the final product in order to obtain the desired dinitroaniline in its purified form.

Many denitrosation processes are described in the patent literature. One of the most frequently used denitrosation agents is sulphamic acid, used together with strong acids such as, for example, hydrochloric acid or with aqueous hydrobromic acid.

Italian patent number 1,104,815, which corresponds to U.S. Pat. No. 4,134,917, describes a method for the denitrosation of dinitroanilines using a ketone or aldehyde in the presence of hydrochloric or hydrobromic acid. Even though the denitrosation can be conducted in the absence of a solvent in the organic phase, in the embodiments the reaction is always conducted in the presence of the solvent utilised for the dinitration, typically dichloroethane. At the end of the denitrosation reaction in the presence of solvent, the reaction mixture is adjusted to pH 10 using sodium hydroxide to form a solid which is then separated by filtration.

The denitration reaction is described in EP-A-0 024 503 and EP-A-0 049 384. The method described therein is carried out on a nitration mixture comprising a solution of the desired dinitroaniline and the corresponding unwanted impurities N-nitro- and N-nitroso-dinitroaniline in a solvent such as dichloroethane, chloroform, carbon tetrachloride or monochlorobenzene which, after having been denitrosated by way of the method described in U.S. Pat. No. 4,134,917 mentioned above, is then subjected to denitration using a phase-transfer catalyst in the presence of an aqueous base such as sodium or potassium hydroxide or carbonate, or ammonium carbonate or hydroxide in sufficient quantity to take the pH to at least 7. The phase-transfer catalysts used include phosphonic salts, symmetrical or asymmetrical ammonium salts, crown ethers, pyrazole salts, hexadecylpyridine salts, and mixtures of anionic or non-ionic emulsifiers. U.S. Pat. No. 4,391,992 also describes the use as a phase-transfer catalyst of onium salts, polyethyleneglycols in which 40 to 50 units of the repetitive $CH_2$–$CH_2O$ group are present, mono- and di-esters of orthophosphonic acid with added ethylene oxide, alkyl-pyridine salts and substituted pyrazole salts. In all cases, the reaction is conducted in the presence of the organic solvent utilised in the nitration reaction.

An object of the present invention is to provide a simplified method for the purification of dinitroanilines, which enables substantial savings from the point of view of both energy consumption and investment costs.

To this end, an object of the invention is a method for the purification of dinitroanilines having herbicidal activity by means of the known reactions of denitrosation using acid, and denitration in a neutral or alkaline environment in the presence of a phase-transfer catalyst, characterised in that the denitrosation reaction is carried out on the dinitration mixture containing the dinitroaniline of interest and the corresponding unwanted impurities N-nitroso- and N-nitro-dinitroanilines in the absence of solvent, and the denitration reaction is conducted sequentially to the denitrosation reaction in the same reactor with the addition to the denitrosation product as such of a base in aqueous solution and of said phase-transfer catalyst.

The method according to the invention is particularly advantageous when carried out on the nitration mixture obtained according to the method described in published European patent application number EP-A-0 847 984 which provides for the continuous dinitration of aromatic substrates in a tubular reactor in the absence of solvent.

Surprisingly, it has been found that by operating under the conditions according to the invention, there is no evident formation of solid following the denitrosation reaction and the addition of the aqueous base, and no filtration operation is therefore necessary before proceeding to the denitration reaction.

On completion of the denitration, the organic phase containing the desired purified dinitroaniline can easily be separated from the aqueous phase to be then subjected to washing steps.

In the method according to the invention, the denitrosation reaction can be conducted following any method known in the literature, for example, using aqueous hydrobromic acid and sulphamic acid; preferably, this reaction is actually carried out using aqueous hydrochloric acid in the presence of a ketone as described in U.S. Pat. No. 4,134,917 and, still more preferably, using diethyl ketone.

The denitrosation reaction is typically carried out under agitation at a temperature of from 57 to 120° C. sufficient to keep the dinitration mixture in a melted state, at atmospheric or superatmospheric pressure, for time sufficient to essentially complete the reaction.

At the end of the reaction, the reaction mixture is kept in the same reactor and the aqueous base added, which base can be chosen from those listed above in relation to the prior art, and which is preferably sodium hydroxide in a sufficient quantity to bring the pH to a value preferably greater than 7, preferably approximately 10–13.

The phase-transfer catalyst can be chosen from any of the catalysts cited in EP-A-0 024 503, EP-A-0 049 384 and U.S. Pat. No. 4,391,992.

In a preferred embodiment, the phase-transfer catalyst is an aliphatic alcohol, or a mixture of linear aliphatic alcohols of the formula: $CH_3(CH_2)_n(OC_2H_4)_mOH$, where n is an integer between 11 and 14, and m an integer between 30 and 40. The quantity of the phase-transfer catalyst is not particularly critical and can be determined by the skilled in the art depending on the catalyst used; typically, this quantity is between 0.8 and 3 moles per mole of N-nitro-dinitroaniline. The dinitration reaction is conducted under energetic agitation for a typical time of from approximately 10 minutes to approximately 3 hours at a temperature sufficient to keep the reaction mass in the melted state.

EXAMPLE 1

50.2 g of the dinitration product, containing 81% of Pendimethalin, 13% of N-nitroso-Pendimethalin, and 700 ppm of N-nitro-Pendimethalin are added to a 250 ml balloon flask provided with a cooler, a thermometer and under mechanical agitation. 9.0 g of 32% aqueous, HCl and 1.64 g of diethylketone are added, and heated to 85° C. in a bath under energetic agitation for 4.5 hours. 59.6 g of 10% aqueous NaOH and 0.25 g of benzyltriethylammonium chloride are then added, and maintained under energetic agitation for a further two hours. The phases are separated and the organic layer washed energetically twice with 30 ml of water preheated to 75° C. 49.7 g of the organic phase are recovered, which solidifies on cooling and which contains 93.3% Pendimethalin, 37 ppm N-nitroso-Pendimethalin and 9 ppm N-nitro-Pendimethalin.

EXAMPLE 2

51.4g of the dinitration product containing 81% by weight of Pendimethalin, 13% by weight of N-nitroso-Pendimethalin and 700 ppm of N-nitro-Pendimethalin are added to a 250 ml balloon flask provided with refrigerant, a thermometer and under mechanical agitation. 9.0 g of 32% aqueous HCl and 1.64 g of diethylketone are added and the mixture heated to 85° C. in a bath under energetic agitation for 4.5 hours. 61.2 g of 10% of aqueous NaOH and 0.91 g of M30 (a linear chain ethoxylated aliphatic alcohol of the formula $CH_3(CH_2)_n(OC_2H_4)_mOH$, where n is between 11 and 14, and m is between 30 and 40) are then added.

This is maintained under energetic agitation for a further two hours. The phases are separated and the organic layer washed energetically two times with 30 ml of water heated to 75° C. 50.8 g of the organic phase are recovered which solidify on cooling and which contain 93.6% Pendimethalin, 32 ppm N-nitroso-Pendimethalin and 17 ppm N-nitro-Pendimethalin.

EXAMPLE 3

The method described in example 1 is repeated, adding 49.8 g of the aforesaid dinitration product to the balloon flask. The denitrosation reaction is conducted as in example 1 by adding 9.1 g of 32% aqueous HCl and 1.61 g diethylketone. On completion of the reaction, 60.0 g of 10% aqueous NaOH and 0.5 g of 18-Crown-6 are added, and this maintained under energetic agitation for a further two hours. After phase separation and washing, as in example 1, 48.8 g of the organic phase are recovered and solidified by cooling, containing 93.2% by weight of Pendimethalin, 42 ppm N-nitroso-Pendimethalin and 12 ppm N-nitro-Pendimethalin.

EXAMPLE 4

400 g of dinitration product, the composition by weight of which is given in table 1, are added to a one liter jacketed reactor, mechanically agitated and provided with a reflux cooler. 6.6 g of diethylketone are added and the temperature maintained at 70° C. 56 g of 32% aqueous HCl solution are added and the mixture taken to 85° C. and agitated energetically for 4.5 hours. The reduction of the N-nitroso-Pendimethalin over time is given in table 1. At the end, 220 g of 10% aqueous NaOH solution and 1 g of benzyltriethyl ammonium chloride are added, agitating for a further 1.5 hours. The agitation is stopped, the reactor cooled to 70° C. and the phases separated. The organic phase is washed two times using 65 g of demineralised water heated to 70° C. 396 g of organic phase are recovered which solidify on cooling and which, on analysis, are shown to contain 93.9% by weight of Pendimethalin, 40 ppm N-nitroso-Pendimethalin and less than 10 ppm N-nitro-Pendimethalin.

TABLE 1

|  | Initial Content | 1 h | 2 h | 4.5 h | 6.5 h |
| --- | --- | --- | --- | --- | --- |
| Pendimethalin | 79.6% | 89.4% | 92.5% | 94.0% | 93.9% |
| N-nitroso-Pendimethalin | 15.2% | 5.3% | 2.1% | 38 ppm | 40 ppm |
| N-nitro-Pendimethalin | 0.89% | 0.89% | 0.88% | 0.88% | <10 ppm |

What is claimed is:

1. A method for the purification of dinitroanilines having herbicidal activity by means of the known reactions of denitrosation using acid, and denitration in a neutral or basic environment in the presence of a phase-transfer catalyst, wherein:

a. the denitrosation is effected on the dinitration mixture containing the dinitroanilines of interest and corresponding unwanted impurities of N-nitroso- and N-nitro-dinitroanilines, at a temperature sufficient to keep the said dinitration mixture in the melted state, and in the absence of solvent; and b. the denitration reaction is conducted sequentially to the denitrosation reaction in the same reactor with the addition to the denitrosation product of an aqueous base and of said phase-transfer catalyst.

2. A method according to claim 1, wherein the denitrosation reaction is effected using aqueous hydrochloric or hydrobromic acid in the presence of a ketone or aldehyde.

3. A method according to claim 1, wherein the denitrosation reaction is effected using sulphamic and aqueous hydrobromic acid.

4. A method according to any of claims 1 to 3, in which the denitration reaction is effected with the addition of an aqueous alkaline base having a pH greater than 7.

5. A method according to claim 4, wherein the phase-transfer catalyst used is an aliphatic alcohol or a mixture of linear chain aliphatic alcohols having the formula $CH_3(CH_2)_n(OC_2H_4)_mOH$, where n is an integer between 11 and 14, and m is an integer between 30 and 40.

6. A method according to claim 1 in which the desired dinitroaniline is Pendimethalin.

* * * * *